United States Patent [19]

Ramer

[11] Patent Number: 4,579,558

[45] Date of Patent: Apr. 1, 1986

[54] MECHANICAL HIP JOINT

[76] Inventor: James L. Ramer, Rte. one, Box 51, Fortuna, Mo. 65034

[21] Appl. No.: 569,643

[22] Filed: Jan. 10, 1984

[51] Int. Cl.⁴ .............................................. B62D 57/02
[52] U.S. Cl. ........................................ 901/28; 901/18; 403/56; 403/122; 623/22; 623/31
[58] Field of Search ......................... 3/1.1, 1.91, 1.911, 3/1.912, 1.913, 14, 15, 16, 17, 30, 31, 32, 33; 901/28, 23, 29, 14, 15, 18; 414/735, 733; 180/8.6, 8.1; 446/355; 403/56, 57, 122; 128/80 F, 800; 434/274

[56] References Cited

U.S. PATENT DOCUMENTS

| | | | |
|---|---|---|---|
| 3,663,967 | 5/1972 | Vermillion | 3/15 |
| 3,982,281 | 9/1976 | Giliberty | 3/1.913 |
| 4,216,550 | 8/1980 | Thompson | 3/15 |
| 4,261,113 | 4/1981 | Alderson | 434/274 |
| 4,324,302 | 4/1982 | Rabinovitch | 180/8 C |

OTHER PUBLICATIONS

Raibert and Sutherland, "Machines That Walk", Jan. 1983, *Scientific American;* pp. 44-53.

*Primary Examiner*—Richard J. Apley
*Assistant Examiner*—James Prizant
*Attorney, Agent, or Firm*—Donald J. Singer; Bobby D. Scearce

[57] ABSTRACT

A novel mechanical hip joint for attaching a robotic leg to a body member is described, which comprises, a housing adapted for connection to the body member, a spherical socket defined within the housing, a ball joint received by the socket for rotational movement about a first horizontal axis, a bearing member rigidly interconnecting the leg and the ball joint and presenting a bearing surface confronting the housing and socket, and a motor interconnecting the housing and bearing surface for selectively imparting rotary movement to the leg, about a second horizontal axis transverse of said first axis, between first and second angular limits.

7 Claims, 9 Drawing Figures

U.S. Patent  Apr. 1, 1986  Sheet 1 of 3  4,579,558
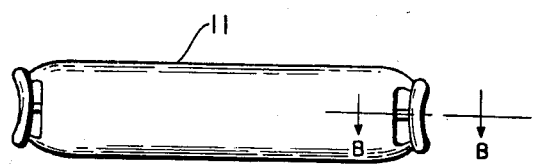
_Fig. 1a_
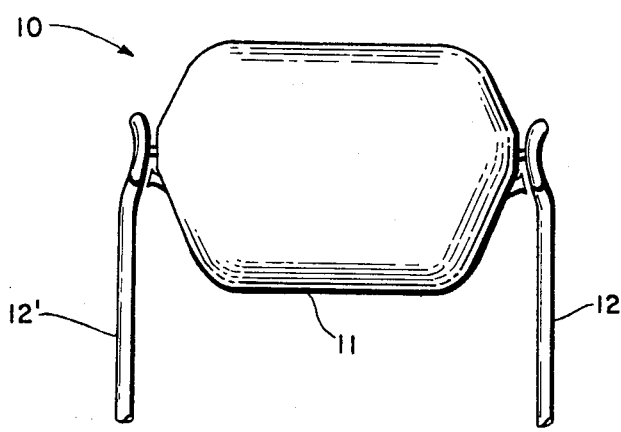
_Fig. 1_
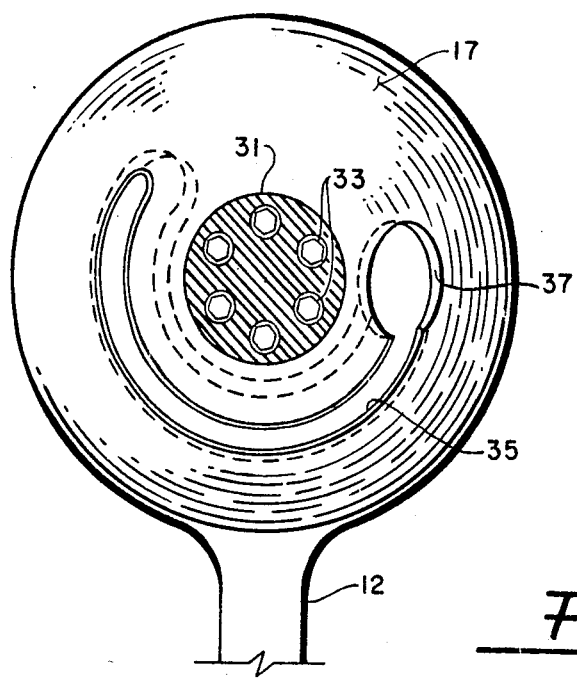
_Fig. 3_

MECHANICAL HIP JOINT

RIGHTS OF THE GOVERNMENT

The invention described herein may be manufactured and used by or for the Government of the United States for all governmental purposes without the payment of any royalty.

BACKGROUND OF THE INVENTION

The present invention relates generally to mechanical joints for robotic devices and the like, and more particularly to an improved mechanical hip joint adaptable for robotic construction.

In the design of articulating joints for use in the construction of robotic devices, duplications of the dynamic and static motions approximating that of the human skeleton are most elusive. For robotic devices including lower supporting limbs, special weight-bearing and articulating performance requirements in the artificial joint are presented. Existing joint devices comprising two articulating surfaces, such as that imitative of a hip joint, may be characterized by materials of construction and by sufficient structural design to adequately carry imposed loads at the various load-bearing surfaces. However, existing devices have been inadequate in providing an articulating joint which both carries anticipated loads against undesirable wear at the articulating surfaces, and allows freedom of movement in all the degrees of freedom which imitate a natural skeletal joint.

The present invention solves or substantially reduces in critical importance the aforementioned problems with existing devices by providing an improved mechanical hip joint for use in robotic construction.

It is, therefore, a principal object of the invention to provide an improved mechanical hip joint for robotic construction.

It is a further object of the invention to provide a mechanical hip joint which closely simulates a natural joint in function and movement.

These and other objects of the present invention will become apparent as the detailed description of certain representative embodiments thereof proceeds.

SUMMARY OF THE INVENTION

In accordance with the foregoing principles and objects of the present invention, a novel mechanical hip joint for attaching a mechanical leg to a body member of a robotic device is described, which comprises, a housing adapted for connection to the body member, a spherical socket defined within the housing, a ball joint received by the socket for rotational movement about a first horizontal axis, a bearing member rigidly interconnecting the leg and the ball joint and presenting a bearing surface confronting the housing and socket, and a motor interconnecting the housing and bearing surface for selectively imparting rotary movement to the leg, about a second horizontal axis transverse of said first axis, between first and second angular limits.

DESCRIPTION OF THE DRAWINGS

The present invention will be more clearly understood from a reading of the following detailed description in conjunction with the accompanying drawings wherein:

FIG. 1 is a schematic elevational view of the hip region of a robotic mechanism incorporating the mechanical hip joint of the present invention.

FIG. 1a is a top view of the mechanism of FIG. 1.

FIG. 3 is a sectional view of FIG. 2 taken along lines C—C.

DETAILED DESCRIPTION

Referring now to the accompanying drawings, FIG. 1 presents a schematic elevational view of the hip region of a robotic mechanism 10 incorporating the mechanical hip joint of the present invention. The hip joints are supported within a structural member or housing 11 and supported on a pair of robotic legs 12, 12'. FIG. 1a is a top view of mechanism 10.

Figure 2:
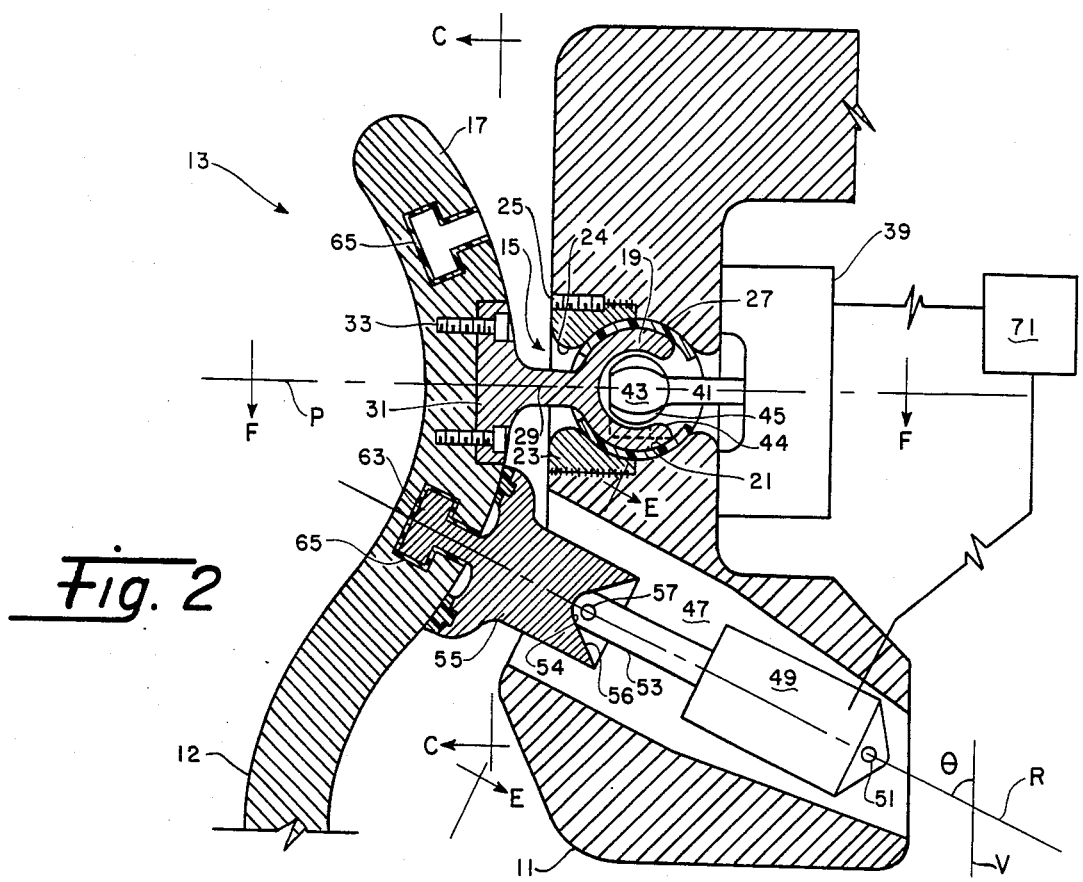
FIG. 2 presents a vertical sectional view of the hip joint of the present invention in the left side configuration.

FIG. 2 presents a schematic back view, in section, of the left hip embodiment of the present invention, together with motorized components and mechanical linkages useful in its operation. FIG. 2 may also be viewed as a section of FIG. 1a taken along lines B—B. The hip joint rotary mechanism 13 of the present invention may be supported for rotation within the supporting structural member 11. Structural member 11 is analogous in a robotic structure to a human pelvis; structural member 11 is sized and configured to house and support the necessary internal mechanical linkages and controls for the articulating parts, and to carry the loads that may be imposed upon the hip joint in robotic application. A leg member 12 may be attached to structural member 11 for rotation about a pair of axes using the novel rotary ball-and-socket hip structure indicated generally at 15. Leg 12 terminates at the top thereof in an enlarged curvilinear surface portion sized to provide a bearing surface 17 to support the hip joint mechanism as hereinafter described.

Hip structure 15 comprises a generally spherically-shaped, hollow ball 19, and a generally spherical socket 21 defined within structural member 11. Ball 19 is restrained within socket 21 using an externally threaded ring member 23 having a central opening 24, the ring member 19 being held against backing out of assembly with structural member 11 by a threaded locking key 25. It is important to note that the center of rotation of the hip joint 13 about any axis herein defined is the center of ball 19 and socket 21. The internal bearing surface defining socket 21 is coated with a high impact resistant, resilient elastomeric material layer 27 that exhibits a low characteristic coefficient of expansion and a low coefficient of friction with ball 19. A typical nonlimiting elastomeric material preferred for this application, as well as for application to other articulating, load-bearing surfaces of the invention as hereinafter described may be Teflon ®, although numerous other elastomeric coatings may be used as might occur to one with skill in the applicable field. Ball 19 may preferably comprise hardened and highly polished steel. Ball 19 has an appending member in the form of neck 29 and attached base 31 projecting through opening 24 in ring 23 for attachment to surface 17 of leg 12 by way of screws 33. The exposed surfaces of neck 27 and base 31 are smoothed and screws 33 are preferably countersunk substantially as shown in FIG. 2 to provide a smooth, flush, continuous surface with leg bearing surface 17.

Referring now to FIG. 3, which is a sectional view of FIG. 2 taken along lines C—C thereof, it is seen that the upper portion of leg 12 and defining bearing surface 17 may preferably be generally circular in shape. Cut into the surface 17 in a circular configuration concentric with base 31 (and neck member 29 connected to ball 19) is a groove 35 in the shape of an inverted "T". Groove 35 subtends an angle of about 145° concentric with base 31, and terminates at one end with an enlargement in the form of opening 37, substantially as shown in FIG. 3, for inserting a component of the hip mechanism as hereinafter described.

A hydraulic or electric motor 39 may be mounted to or within structural member 11 substantially as shown in FIG. 2 in order to provide a source of power for moving leg 12. A power shaft 41 is used to drive a splined or hexagonal surface drive ball 43 about axis P; ball 43 is enclosed within the cavity defined within hollow ball 19. Ball 19 has on its inner surface and contacting drive ball 43 hex or splined surfaces which contact mating surfaces 45 on drive ball 43, to effectively transmit torque through ball 19 to leg 12. Drive ball 43 is preferably enveloped within ball 19 in a substantial wrap-around configuration such that drive ball 43 is nonremovable from ball 19 once manufactured and assembled. Shaft 41 may preferably be in the form of a floating male insert within a mating female cavity on motor 39. This configuration may provide for ease of changing worn or broken components, e.g., ball 19, drive ball 43, shaft 41 or any connecting mechanisms.

In the embodiment of FIG. 2, lateral movement to leg 12 in a vertical plane (i.e., in the plane of FIG. 2) and about a horizontal axis H through ball 19 and perpendicular to the plane of FIG. 2, may be imparted through a motor driven ram configuration mounted within structural member 11 and acting on leg 12 at points eccentric to the central connection at base 31. In order to accommodate the driving mechanism, a rectangularly-shaped recess 47 may be provided in structural member 11 substantially as shown. A double acting linear motor 49 is mounted to structural member 11 within recess 47 through a pin 51 in order to impart movement to a ram 53, substantially along an axis R, for movement of leg 12 in the vertical plane, axis R, along which recess 47 within structural member 11 is defined, being defined at any convenient angle $\theta$ for imparting the desired motion to leg 12. Ram 53 has a rounded end surface 54 and is connected to a ram-bearing block 55 via a pin 57 located in a recess 56 in block 55 substantially as shown.

Figure 4:
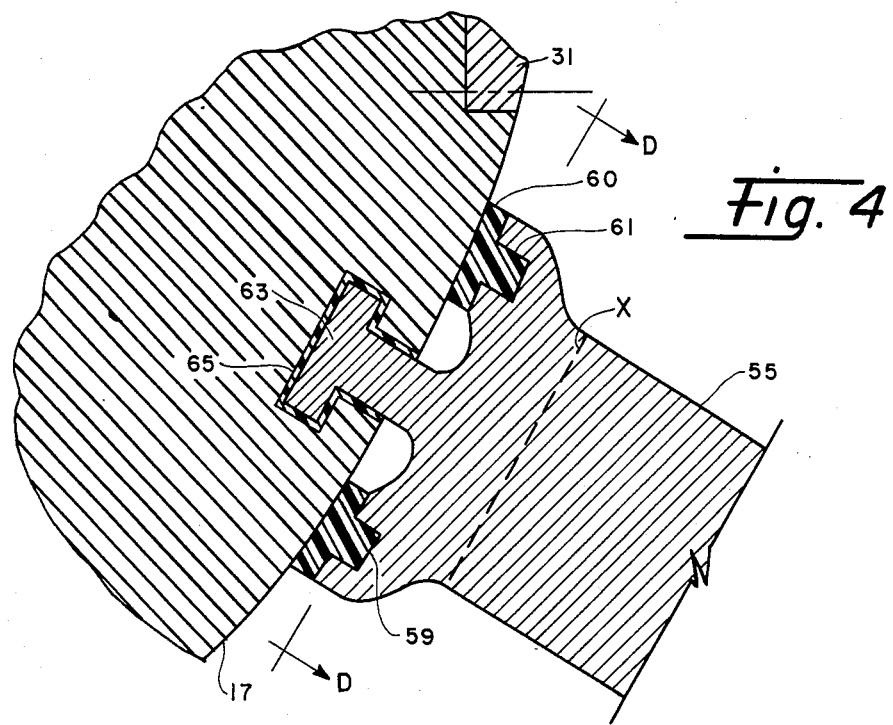
FIG. 4 is an enlarged view of a portion of FIG. 2.
Figure 5:
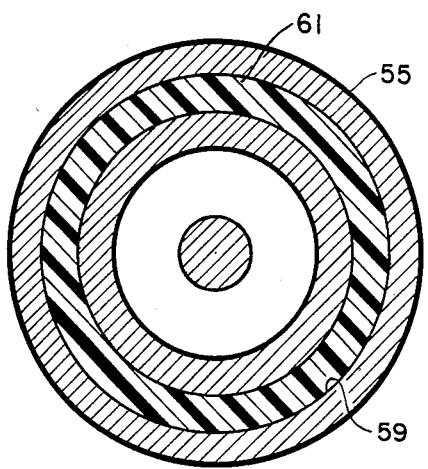
FIG. 5 is a sectional view of FIG. 4 taken along lines D—D.
Figure 6:
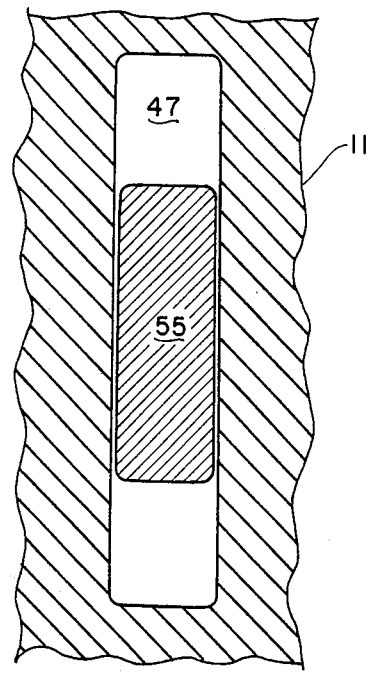
FIG. 6 is a sectional view of FIG. 2 taken along lines E—E.

With reference to FIG. 4, which is an enlarged view of the region of FIG. 2 where bearing block 55 engages surface 17, it is seen that the section of the block 55 bearing against surface 17 of leg 12 is circular, as shown in more detail in FIG. 5, which is a view of FIG. 4 taken along lines D—D. Block 55 has an annular groove 59 for receiving an annular tab 61 of gasket 60 as shown in FIGS. 4 and 5. Gasket 60 provides a bearing and wearing surface between block 55 and the bearing surface 17 and comprises an elastomer having low coefficients of friction and expansion, and high impact resistance, similar to that preferred for layer 27 which lines socket 21. The circular portion of block 55 transitions to the rectangular shape, such that a completely rectangular section of the desired size to fit within recess 47 may be defined at about point "X" as indicated on the enlarged view in FIG. 4. The shape of block 55 is illustrated more clearly in FIG. 6, which is a sectional view of FIG. 2 taken along lines E—E. The surface of the rectangular portion of bearing block 55 and the confronting surface defining rectangular recess 47 may preferably comprise hardened steel with a permanent solid lubricant coating of such as Teflon ® applied thereon. The positive connections provided by pinned connections 51 and 57, and a matching of the surface 54 of ram 53 with the mating recess 56 in block 55 allows for a complete engagement of the elastomeric gasket 60 against bearing surface 17 when leg 12 is oriented anywhere within its designed mechanical limits. Positive sliding engagement of block 55 with bearing surface 17 of leg 12 is provided by a circular projection 63 having a T-shaped axial cross section, attached to or integral with block 55 substantially as shown in FIGS. 2 and 4. Projection 63 is configured to ride in groove 35 of bearing surface 17 (see also FIG. 3). Groove 35 may be lined with an elastomeric bearing layer 65 (similar to layer 27 of FIG. 2) to provide the desired sliding engagement of projection 63 with groove 35. As discussed above in relation to FIG. 3, groove 35 has at one end thereof a circular enlargement 37 which allows insertion of the projection 63 thereinto for sliding attachment of leg 12 to bearing block 55.

Figure 8:
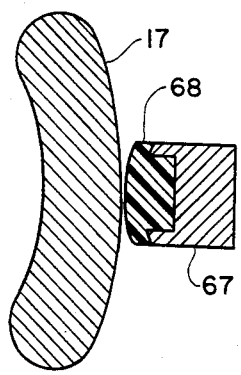
FIG. 8 is a sectional view of FIG. 7 taken along lines G—G.
Figure 7:
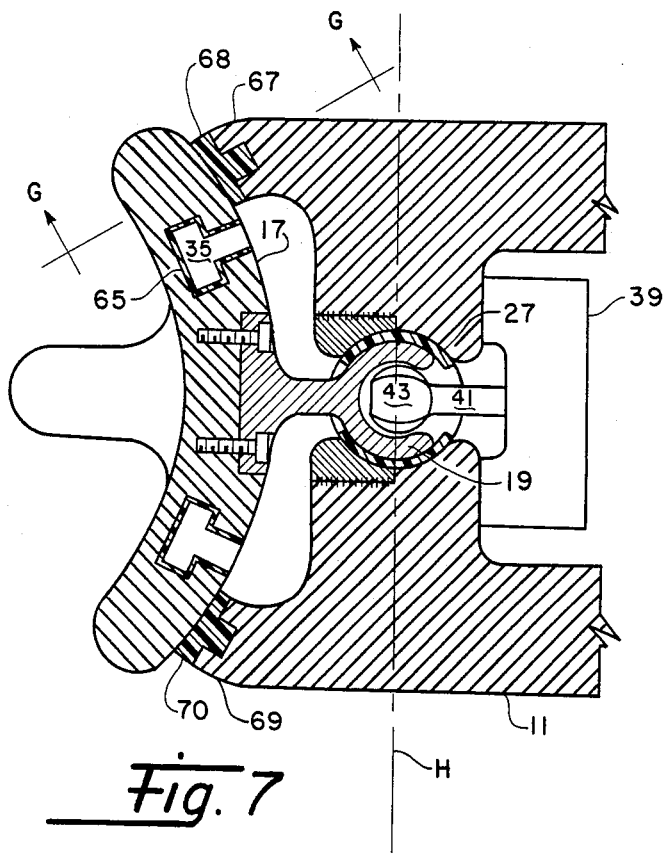
FIG. 7 is a sectional view of FIG. 2 taken along lines F—F.

Referring now to FIG. 7, which is a view of FIG. 2 taken along lines F—F thereof, member 11 has suitable shape to define a front stop 67 and rear stop 69 in order to prevent horizontal rotation of leg 12 about a vertical axis through ball 19. Resilient elastomeric stop pads 68 front and 70 rear comprise an elastomer having properties similar to that described as used elsewhere herein. Stop pads 68 and 70 provide a bearing and wearing surface between the bearing surface 17 and the front and rear stops 67,69. The front stop 67 and rear stop 69 are rounded on a vertical arc concentric with the center of ball socket 21 as shown in FIG. 8, which is a view of FIG. 7 taken along lines G—G. This rounding allows for lateral rotary motion of leg 12 (around axis H), but prevents horizontal rotary motion (about a vertical axis V through ball 19). This ensures that the knee, ankle and foot elements (not shown) which may be connected to leg 12 remain aligned in a proper geometric attitude when the robotic system incorporating the hip joint 13 of the present invention is either moving or at rest.

In the operation of hip joint 13 as a robotic mechanism, rotary motion of leg 12 in a vertical plane about axis P is imparted by motor 39 controlled by suitable limiting switches or valves that preferably limit angular movement of the leg 12 connected to the bearing surface 17 from about 120° forward to about 25° rearward relative to a vertical. The magnitude of the angular movement of leg 12 about axis P is limited by the length of groove 35 defined within surface 17, and the rotary limits of switches or valves controlling motor 39. Driving torque is transmitted to the leg 12 through shaft 41, splined ball 43, and ball 19.

Lateral rotary motion of leg 13 in a vertical plane about horizontal axis H (see FIG. 7) is provided by the linear motor 49-ram 53-block 55 configuration previously described. For the configuration described in the drawings, lateral rotary motion of leg 13 outward (away from housing 11) or inward relative to a vertical plumb line will ordinarily be about the same as attainable for a human, limited only by the degree to which ball 19 envelopes drive ball 43 and limit switches or valves controlling the motive power to linear motor 49. The right and left lateral rotary movement of the leg 12 is therefore unrestricted within anticipated limits due to the ability of all component parts to follow the forward and rearward rotary motion in the vertical plane of the leg-bearing surface 17 as leg 12 is propelled in the vertical plane by motor 39. This following ability is a result of the enlarged vertical clearances provided in the rectangular recess 47, the positive connections provided by pinned connections 51,57 and the engagement of the elastomeric gasket 60 against bearing surface 17 at any leg 12 position during vertical or lateral rotary motion or a combination thereof. In like manner, complete engagement against leg-bearing surface 17 by the gasket 60 is provided by the positive engagement of projection 63 within the groove 35.

The circular enlargement opening 37 that allows insertion of the projection 63 into groove 35 is positioned such that for maximum anticipated rotary motion of the leg 12 in the vertical plane, i.e., 120° forward and 25° rearward, projection 63 is not interferred with by enlargement 37 as it rides in groove 35, but allows for the hip mechanism 15 and leg 12 to be assembled (or disassembled) by manually rotating the leg 12 to the point where projection 63 meets opening 37, and then inserting (or removing) projection 63 into (or from) groove 35.

The motors 39,49 may be suitably controlled by switching and control means of substantially conventional design, shown schematically as controller 71, in order to provide movement to leg 12 in the various degrees of freedom corresponding to rotation about axes P and H.

The present invention, as hereinabove described, provides a novel mechanical hip joint for robotic application. It is understood that certain modifications to the invention as described may be made, as might occur to one with skill in the field of this invention, within the scope of the appended claims. Therefore, all embodiments contemplated hereunder have not been shown in complete detail. Other embodiments may be developed without departing from the spirit of this invention or from the scope of the appended claims.

I claim:

1. An articulating mechanical hip joint for attaching a robotic leg to a body member, comprising:
   a. a housing adapted for connection to said body member, said housing defining a first substantially spherically shaped socket therein, and a ball joint, received by said socket, for rotational movement thereof within said housing and socket about a predetermined first horizontal axis;
   b. a bearing member, rigidly interconnecting said leg and ball, said bearing member defining a bearing surface confronting said housing and socket and constrained for rotational movement with said ball about said first horizontal axis; and
   c. means, interconnecting said housing and said bearing member, for selectively rotating said leg and bearing member about a second horizontal axis, defined through said ball and transverse of said first horizontal axis, between predetermined first and second angular limits.

2. The mechanical hip joint as recited in claim 1 further comprising a motor mounted to said housing and operatively interconnected with said ball joint for selectively imparting rotary movement to said leg by rotating said ball joint about said first horizontal axis.

3. The mechanical hip joint as recited in claim 1 further comprising stop means on said housing for limiting the rotational movement of said bearing member about a vertical axis defined through said ball.

4. The mechanical hip joint as recited in claim 1 wherein said bearing surface is substantially spherical in shape.

5. The mechanical hip joint as recited in claim 1 wherein said means interconnecting said housing and said bearing member comprises a bearing block slideably attached to said bearing member, and linear motor means, pivotally interconnecting said bearing block and said housing, for imparting movement to said block between first and second limits corresponding to said predetermined first and second angular limits of movement of said leg about said second horizontal axis.

6. The mechanical hip joint as recited in claim 5 wherein said linear motor means is mounted in a cavity defined within said housing below said ball joint.

7. The mechanical hip joint as recited in claim 5 wherein said bearing member has defined therein an annular groove substantially concentric with said first horizontal axis, and said bearing block includes a projection thereon slideably received by said groove.

* * * * *